(12) United States Patent
Yoshikawa

(10) Patent No.: US 7,153,592 B2
(45) Date of Patent: Dec. 26, 2006

(54) ORGANIC EL ELEMENT AND METHOD OF MANUFACTURING THE SAME, ORGANIC EL DISPLAY DEVICE USING THE ELEMENT, ORGANIC EL MATERIAL, AND SURFACE EMISSION DEVICE AND LIQUID CRYSTAL DISPLAY DEVICE USING THE MATERIAL

(75) Inventor: Kota Yoshikawa, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 209 days.

(21) Appl. No.: 09/916,314

(22) Filed: Jul. 30, 2001

(65) Prior Publication Data
US 2002/0051894 A1 May 2, 2002

(30) Foreign Application Priority Data
Aug. 31, 2000 (JP) .............. 2000-262567
Jan. 17, 2001 (JP) .............. 2001-008785

(51) Int. Cl.
H01L 51/50 (2006.01)
H05B 33/14 (2006.01)
H05B 33/26 (2006.01)
C09K 11/06 (2006.01)

(52) U.S. Cl. .............. 428/690; 428/917; 313/502; 313/504; 313/506

(58) Field of Classification Search .............. 428/690, 428/917; 313/502, 504, 506
See application file for complete search history.

(56) References Cited

U.S. PATENT DOCUMENTS

| | | | | |
|---|---|---|---|---|
| 3,888,673 A | * | 6/1975 | Suzuki et al. .............. 430/24 |
| 4,647,518 A | * | 3/1987 | Matsuda .............. 430/21 |
| 5,811,834 A | * | 9/1998 | Tamano et al. .............. 257/40 |
| 6,037,190 A | * | 3/2000 | Chao et al. .............. 438/35 |
| 6,262,441 B1 | * | 7/2001 | Bohler et al. .............. 257/103 |
| 6,310,231 B1 | * | 10/2001 | Igarashi et al. .............. 556/489 |
| 6,361,917 B1 | * | 3/2002 | Kang et al. .............. 430/139 |
| 6,459,199 B1 | * | 10/2002 | Kido et al. .............. 313/504 |
| 6,501,218 B1 | * | 12/2002 | Duggal et al. .............. 313/510 |
| 6,656,608 B1 | * | 12/2003 | Kita et al. .............. 428/690 |
| 2001/0001050 A1 | * | 5/2001 | Miyashita et al. .......... 428/690 |
| 2001/0041268 A1 | * | 11/2001 | Arai et al. .............. 428/690 |
| 2002/0121638 A1 | * | 9/2002 | Grushin et al. .............. 257/40 |
| 2003/0166810 A1 | * | 9/2003 | Holmes et al. .............. 526/256 |

FOREIGN PATENT DOCUMENTS

| | | |
|---|---|---|
| EP | 0745658 A1 * | 12/1996 |
| JP | 7-169567 | 7/1995 |
| JP | 11-067459 A * | 3/1999 |

OTHER PUBLICATIONS

Lee et al., Synthetic Metals, 105 (1999), p. 185-190.*
Li et al., Advanced Materials, (1995), vol. 7, No. 11, p. 898-900.*

* cited by examiner

Primary Examiner—Dawn Garrett
(74) Attorney, Agent, or Firm—Armstrong, Kratz, Quintos, Hanson & Brooks, LLP

(57) ABSTRACT

In an organic EL element, an organic EL layer is interposed between anodes and cathodes formed on a substrate. Each of the cathodes is made of a first conductive film that comes into contact with the organic EL layer and a second conductive film that constitutes a laminated structure together with the first conductive film. The first conductive film contains any one of an alkaline metal and an alkaline earth metal. The second conductive film contains any one of at least one type metal selected from a group consisting of Ru (ruthenium), Rh (rhodium), Ir (iridium), Os (osmium) and Re (rhenium) and its oxide.

4 Claims, 6 Drawing Sheets

ORGANIC EL ELEMENT AND METHOD OF MANUFACTURING THE SAME, ORGANIC EL DISPLAY DEVICE USING THE ELEMENT, ORGANIC EL MATERIAL, AND SURFACE EMISSION DEVICE AND LIQUID CRYSTAL DISPLAY DEVICE USING THE MATERIAL

BACKGROUND OF THE INVENTION

1. Field of the Invention

The present invention relates to an organic EL (Electroluminescence) element having a structure in which an organic EL layer is put between a pair of electrodes, an organic EL display device employing the element, organic EL material, and a plane emission device and a display device employing the material.

2. Description of the Prior Art

In recent years, the organic EL element (the organic LED) is well appreciated as the spontaneous emission element. The organic EL element has the advantage that such element can be driven by the low voltage rather than the inorganic EL element and also the advantage that such element can be manufactured without complicated manufacturing processes in contrast to the inorganic LED in the prior art.

Also, in comparison with the liquid crystal display device that is widely used at present as the display of the mobile device, the organic EL element has a quick response speed, has a simple device structure, and needs no back-light. Therefore, the organic EL element has the advantage that such element can be reduced in weight. In addition, since the organic EL element is the solid state element, such element has the merit that it is resistant to the impact.

The organic EL element has the structure that the EL emission layer (the organic EL layer) is put between the cathode and the anode. The metal having the large work function is employed as the anode and the metal having the small work function is employed as the cathode, so that supplies of the hole and the electron can be made smooth. Normally, ITO (Indium-Tin Oxide) as the transparent conductor is employed as the anode.

Also, the metal containing the alkaline metal or the alkaline earth metal such as Na (sodium), Na—K (sodium-potassium) alloy, Mg (magnesium), Li (lithium), Mg/Cu (magnesium/copper) mixture, In (indium), etc. is employed as the cathode.

$Alq_3$, $BeBq_3$, DCM, DPVBi, quinacridone derivative, coumalin, etc., for example, is employed as the EL emission layer. Normally, the monomer EL emission layer is formed by the vacuum evaporation method, and the polymer EL emission layer is formed by the spin coating method. Accordingly, the polymer EL emission layer has the advantage that the film formation is easy and also the mechanical strength is high.

In addition, in order to lower the operating threshold voltage of the organic EL element, the trial for forming the buffer layer on the cathode side or the anode side is made. For example, sometimes the layer made of ruthenium oxide (referred to as "RuO" hereinafter), molybdenum oxide (referred to as "MoO" hereinafter), or vanadium oxide (referred to as "VO" hereinafter) is formed as the buffer layer between the anode and the organic EL layer in the prior art. The layer made of RuO, MoO, or VO is formed by the sputter method.

By the way, if the organic EL element is used for a long time, the luminous efficiency is lowered due to the influence of the oxygen and the moisture and also the defect called the dark spot is caused. This is due to the fact that the alkaline metal or the alkaline earth metal employed as the cathode is easily oxidized.

In Patent Application Publication (KOKAI) Hei 7-169567 as the preceding literature, in order to avoid the degradation of the luminous efficiency of the organic EL element due to the oxygen and the moisture, it is proposed that the laminated body consisting of the anode, the organic EL layer, and the cathode should be covered with the layer formed of material that can adsorb, occlude, or consume the oxygen (referred to as a "sealing layer" hereinafter).

Then, the material such as magnesium oxide, magnesium carbonate, iron oxide, titanium oxide, bentonite, or the like, that is impregnated with platinum, palladium, rhodium, ruthenium, or silver at a concentration of less than 5 wt %, etc. are set forth as the material of the sealing layer.

However, the problems discussed in the following are pointed out in the organic EL element disclosed in the above literature. That is, since the laminated body consisting of the anode, the organic EL layer, and the cathode is covered with the insulating sealing layer, the leading electrode that is extended to the outside of the sealing layer must be provided to the anode and the cathode respectively. As a result, the manufacturing steps become complicated and also the rise of the product cost is brought about.

Also, as described above, sometimes the buffer layer made of RuO, MoO, or VO is formed by the sputter method in order to lower the operating threshold voltage.

However, this method has the drawback that the large unevenness is formed. If it is tried to form the $RuO_2$ layer of 30 nm thickness by the sputter method, for example, the hillock having a height of 50 to 100 nm is locally generated. As a result, there is the possibility that, if the thickness of the organic EL layer is reduced, conversely the short-circuit defect is caused.

In addition, in case the full-color image display device using the organic EL elements is fabricated, the organic EL elements for the red color emission, the organic EL elements for the green color emission, and the organic EL elements for the blue color emission must be aligned in both the horizontal direction and the vertical direction in the predetermined order.

Therefore, the technology for patterning finely the organic EL layers is requested. As the fine pattern technology used in manufacturing the semiconductor device, the lift-off method and the etching method are well known.

However, in the case of the monochromatic image display device, it may be considered that, for example, the upper electrodes (the cathodes) of respective pixels are formed by the lift-off method. But it is difficult to apply the lift-off method to the manufacture of the full-color image display device.

Further, since the organic EL layer is formed of the monomer or polymer organic, such organic EL layer has the drawback that it cannot be worked by the fine pattern technology such as the dry etching, etc.

Moreover, the above organic EL element is noted with interest as the back-light device in place of the cold-cathode lamp that is employed in the liquid crystal display device. The cold-cathode lamp, that is employed as the back-light device in the prior art, has the low luminous efficiency and also occupies about 30% of the overall cost of the liquid crystal display device, which is a factor of the cost up.

The monomer and polymer materials are known as the organic EL material. Normally the film of the monomer EL material can be formed by the vacuum evaporation method, whereas the film of the polymer EL material can be formed by the coating method. Therefore, the polymer EL material is advantageous in manufacturing cost.

Since the back-light device using the polymer organic EL material can be driven by the low voltage, the reduction in the consumption power of the liquid crystal display device can be expected and also the cost down and the reduction in size of the device can be expected rather than the cold-cathode lamp in the prior art.

However, the actual circumstances are that the organic EL material that is available in practical use has not been developed yet.

SUMMARY OF THE INVENTION

Therefore, in view of the above circumstances, it is an object of the present invention to provide an organic EL element and a method of manufacturing the same, that is capable of simplifying its manufacturing steps, lowering the product cost, and avoiding the degradation in the luminescence characteristic and the short-circuit defect of an organic EL layer due to the oxygen and the moisture not to cover a laminated body consisting of an anode, the organic EL layer, and a cathode with an insulating sealing layer, and an organic EL display device employing the organic EL element.

Also, it is another object of the present invention to provide organic EL material available in practical use, that can be driven by a low voltage, is capable of achieving the reduction in the power consumption, and achieving the cost down and the reduction in size, and a plane emission device and a display device employing the material.

In order to achieve the above objects, an organic EL element of the present invention comprises:

an organic EL layer formed between an anode and a cathode; and the cathode consisting of a first conductive film that contacts to the organic EL layer and a second conductive film that constitutes a laminated structure together with the first conductive film, the first conductive film containing any one of an alkaline metal and an alkaline earth metal, and the second conductive film containing a metal that is able to prevent entering of an oxygen and a moisture into the first conductive film when the metal is oxidized.

Also, an organic EL element manufacturing method of the present invention comprises the steps of:

forming an anode on a substrate;

forming an organic EL layer on the anodes;

forming a first conductive film, that contains any one of an alkaline metal and an alkaline earth metal, on the organic EL layer; and forming a second conductive film laminated on the first conductive film and containing a metal that is able to prevent entering of an oxygen and a moisture into the first conductive film when the metal is oxidized.

Also, an organic EL element of the present invention comprises:

an anode;

a buffer layer which is formed of at least one type metal selected from a group consisting of Ru, Mo, and V on the anode and a surface of which is oxidized;

an organic EL layer formed to be contacted to an oxidized surface of the buffer layer; and a cathode formed on said organic EL layer.

Also, an organic EL element manufacturing method of the present invention comprises the steps of:

forming an anode on a substrate;

forming a buffer layer, which contains at least one type metal selected from a group consisting of Ru, Mo, and V, on the anode;

oxidizing a surface of the buffer layer;

forming an organic EL layer on the buffer layer; and forming a cathode.

Also, an organic EL display device of the present invention comprises:

a substrate;

a lower electrode formed on the substrate;

an organic EL layer formed on the lower electrode to have areas in which a conjugate length of polymer is different each other so that these areas have two different luminous colors or more; and an upper electrode formed on the organic EL layer.

Also, an organic EL display device manufacturing method of the present invention comprises the steps of:

forming a first electrode on a substrate;

forming an organic EL layer formed of organic EL material, in which a conjugate length of polymer is changed in response to light irradiation, on the first electrode;

irradiating partially a light onto the organic EL layer to change the conjugate length; and forming a second electrode on the organic EL layer.

Further, in order to achieve the above objects, organic EL material of the present invention consists of:

material made of organic material expressed by a general formula (1)

$$\left(\begin{array}{c} O(CH_2)_nO-X-\overset{N-N}{\underset{O}{\diagdown\diagup}}-Y-O(CH_2)_kCH_3 \\ A-C=C \\ | \quad | \\ H \quad H \\ OC_mH_{2m+1} \end{array}\right)_l \quad (1)$$

(Where A is a residue obtained by removing at least four hydrogen atoms from an aromatic compound or a heterocyclic compound, X is an atomic group to which at least two groups that are selected from a group consisting of a residue obtained by removing at least two hydrogen atoms from benzene and a residue obtained by removing at least two hydrogen atoms from cyclohexane are bonded, Y is an atomic group to which a residue obtained by removing at least two hydrogen atoms from benzene is bonded or at least two residues each obtained by removing at least two hydrogen atoms from benzene are bonded, and k, m and n are an integer respectively.)

Also, a plane emission device employing organic material of the present invention, comprises:

a transparent substrate;

a transparent conductive film for covering one surface of the transparent substrate;

an alignment film formed on a surface of the transparent conductive film;

a luminous layer made of organic material expressed by a general formula (2)

$$\left(\begin{array}{c} O(CH_2)_nO-X-\overset{N-N}{\underset{O}{\diagdown\diagup}}-Y-O(CH_2)_kCH_3 \\ A-C=C \\ | \quad | \\ H \quad H \\ OC_mH_{2m+1} \end{array}\right)_l \quad (2)$$

(Where A is a residue obtained by removing at least four hydrogen atoms from an aromatic compound or a heterocyclic compound, X is an atomic group to which at least two groups that are selected from a group consisting of a residue obtained by removing at least two hydrogen atoms from benzene and a residue obtained by removing at least two hydrogen atoms from cyclohexane are bonded, Y is an atomic group to which a residue obtained by removing at least two hydrogen atoms from benzene is bonded or at least two residues each obtained by removing at least two hydrogen atoms from benzene are bonded, and k, m and n are an integer respectively.); and an electrode layer formed on a surface of the luminous layer.

Also, a display device employing organic material of the present invention, comprises:

a transparent substrate;

a transparent conductive film for covering one surface of the transparent substrate;

an alignment film formed on a surface of the transparent conductive film;

a luminous layer made of organic material expressed by a general formula (3)

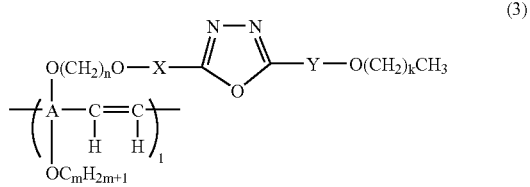

(3)

(Where A is a residue obtained by removing at least four hydrogen atoms from an aromatic compound or a heterocyclic compound, X is an atomic group to which at least two groups that are selected from a group consisting of a residue obtained by removing at least two hydrogen atoms from benzene and a residue obtained by removing at least two hydrogen atoms from cyclohexane are bonded, Y is an atomic group to which a residue obtained by removing at least two hydrogen atoms from benzene is bonded or at least two residues each obtained by removing at least two hydrogen atoms from benzene are bonded, and k, m and n are an integer respectively.);

an electrode layer formed on a surface of the luminous layer;

a liquid crystal layer arranged on a second surface on an opposite side to the first surface of the transparent substrate; and a polarizing plate arranged on the liquid crystal layer.

According to the organic EL element and the method of manufacturing the same of the present invention, the cathode is composed of the first conductive film that contacts to the organic EL layer and the second conductive film formed on the first conductive film, and entering of the oxygen and the moisture into the first conductive film can be prevented by oxidizing the second conductive film.

Therefore, the degradation of the luminous characteristic of the organic EL layer and the generation of the short-circuit defect can be prevented not to cover the laminated body consisting of the anode, the organic EL layer, and the cathode with the insulating sealing layer, and thus the generation of the dark spot can be suppressed for a long time.

Also, according to the organic EL display device manufacturing method of the present invention, the manufacturing steps can be simplified and thus the product cost can be lowered.

Also, according to another organic EL element of the present invention, the buffer layer that contains at least one type metal selected from the group consisting of Ru, Mo, and V is provided between the anode and the organic EL layer, and only the side surface of the buffer layer that contacts to the organic EL layer is oxidized by the short-time annealing, the laser annealing, the plasma oxidation, the anodic oxidation, or the like. Therefore, the unevenness of the surface of the buffer layer is small, and the generation of disadvantages such as the short circuit, etc. can be avoided if the organic EL layer is thinned.

Also, according to the organic EL display device of the present invention, since the areas for emitting the lights in different color by changing the conjugate length of polymer constituting the organic EL layer respectively are formed, the multi-color emission organic EL display device can be easily manufactured.

Also, according to the organic EL material of the present invention, since such organic EL material contains the benzene ring in the principal chain and contains the oxadiazole in the side chain, for example, it can emits the polarized light.

As a result, if the organic EL material of the present invention is employed in the back-light panel, the plane emission device that can be driven by the low voltage and can reduce the power consumption can be obtained. Also, since the display device that is constructed by the back-light panel using the organic EL material, the liquid crystal panel, and the polarizing plate can obtain the polarized light from the luminous layer made of the organic EL material, there is no necessity that the polarizing plate is provided between the back-light panel and the liquid crystal panel and thus the utilization factor of the light can be increased.

DESCRIPTION OF THE PREFERRED EMBODIMENTS

Embodiments of the present invention will be explained with reference to the accompanying drawings hereinafter.

(First Embodiment)

Figure 1:
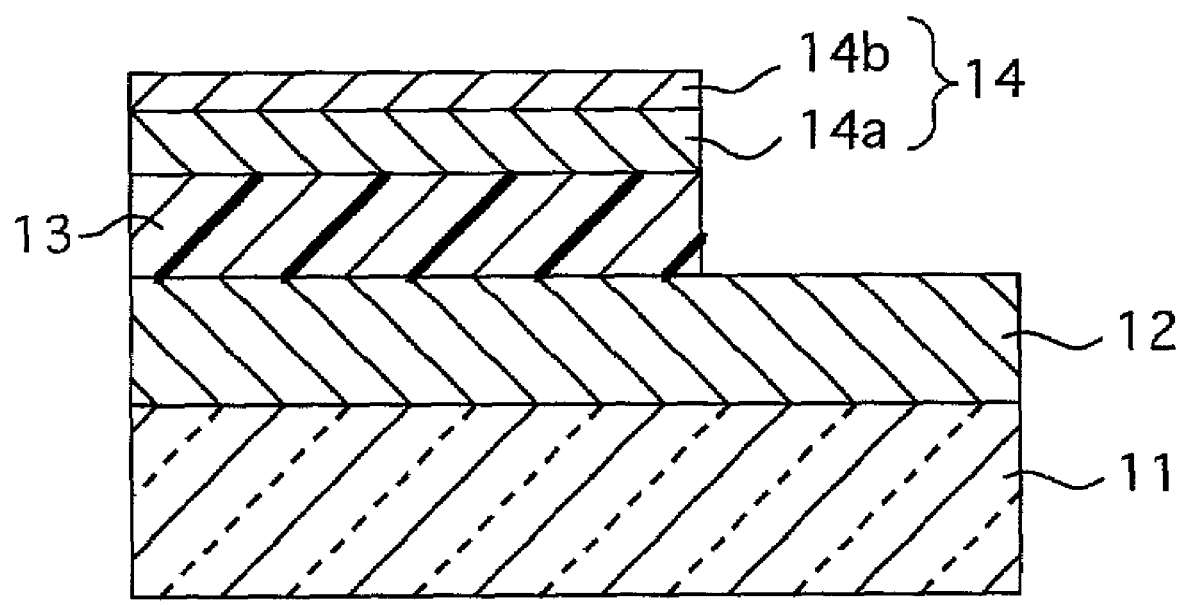
FIG. 1 is a sectional view showing an organic EL element according to a first embodiment of the present invention.

FIG. 1 is a sectional view showing an organic EL element according to a first embodiment of the present invention.

An ITO film of about 200 nm thickness is formed as an anode 12 on a glass substrate 11. Also, a poly[3-(4-alkylphenol)thiophene] film of about 150 nm thickness is formed as an organic EL layer (a luminous layer) 13 in the predetermined area on the anode 12.

In addition, a laminated film having the double-layered structure consisting of a first conductive film 14a made of the conductor containing Mg and a second conductive film 14b made of the conductor containing Ru is formed as a cathode 14 on the organic EL layer 13. In this example, a thickness of the first conductive film 14a is about 100 nm, and a thickness of the second conductive film 14b is about 50 nm.

The anode 12 is not limited to ITO, and any conductor having the large work function may be employed. In this case, if the light is irradiated to the substrate 11 side, the anode 12 must be formed of the conductor that can transmit the light.

The first conductive film 14a may be formed of the conductor containing the alkaline metal or the alkaline earth metal that has the small work function. For example, MgAg, AlLi, LiF, etc. may be employed as the material of the first conductive film 14a. Assume that the first conductive film 14a is formed of MgAg.

Also, the second conductive film 14b is not limited to the conductor containing Ru, and also may be formed of the conductor that has the high barrier characteristic to the oxygen, more particularly, the metal or its oxide selected from the group consisting of Ru, Rh, Ir, Os and Re.

The oxides of Ru, Rh, Ir, Os and Re have also the conductivity. Accordingly, the conductivity of the cathode 14 is never damaged by the oxidation.

In addition, a TiN film or a laminated film consisting of TiN and Ti (referred to as a "TiN/Ti film" hereinafter) may be employed as the second conductive film 14b. These films have also the good barrier characteristic to the oxygen, and can prevent the oxidation of the first conductive film 14a. Also, the conductivity of both the TiN film and the TiN/Ti film is in no way degraded even if they are exposed to the oxygen-containing atmosphere for a long time.

Further, a laminated film consisting of the conductive film, the conductive film containing the metal selected from the group consisting of Ru, Rh, Ir, Os and Re or its oxide, and the TiN film or the TiN/Ti film may be employed as the second conductive film 14b.

In the organic EL element constructed in this manner according to the first embodiment, if the positive voltage is applied to the anode 12 and the negative voltage is applied to the cathode 14, the organic EL layer can emit the light.

In the first embodiment, since the second conductive film 14b containing Ru is formed on the first conductive film 14a that contains Mg as the alkaline metal, Ru in the second conductive film 14b is oxidized to prevent the entering of the oxygen into the first conductive film 14a even if the organic EL element is exposed to the atmosphere containing the oxygen or the moisture for a long time. Accordingly, the oxidation in the first conductive film 14a can be avoided.

As a result, in the organic EL element according to the first embodiment, the degradation of the luminescence characteristic due to the oxygen or the moisture can be avoided and also the generation of the dark spot can be suppressed. Also, since the oxidation of the first conductive film 14a can be avoided, the peeling-off between the organic EL layer 13 and the first conductive film 14a can be prevented. In addition, there is no necessity that the laminated body consisting of the anode 12, the organic EL layer 13, and the cathode 14 should be covered with the insulating material, and thus the manufacture of the element can be facilitated.

A method of manufacturing the organic EL element according to the first embodiment will be explained hereunder.

First, the ITO film of about 200 nm thickness is formed on the overall upper surface of the glass substrate 11 by the sputter method. Then, the poly[3-(4-alkylphenyl)thiophene] film of 150 nm thickness is formed on the overall upper surface of the glass substrate 11 by the spin coating method, and is used as the organic EL layer 13.

In the first embodiment, the material of the organic EL layer 13 is not limited to the above poly[3-(4-alkylphenyl) thiophene. Various organic EL emission materials of the monomer series or the polymer series may be employed as the organic EL layer 13.

Then, the first conductive film 14a is formed by forming the MgAg film of about 100 nm thickness on the organic EL layer 13 by virtue of the sputter method. Then, the second conductive film 14b is formed by forming the Ru film of about 50 nm thickness thereon.

Then, a pair of terminals that are connected to the anode 12 and the cathode 14 respectively are formed by sputtering the metal such as Au, Al, or the like while using a metal mask. Accordingly, the organic EL element according to the first embodiment can be completed.

Figure 2:
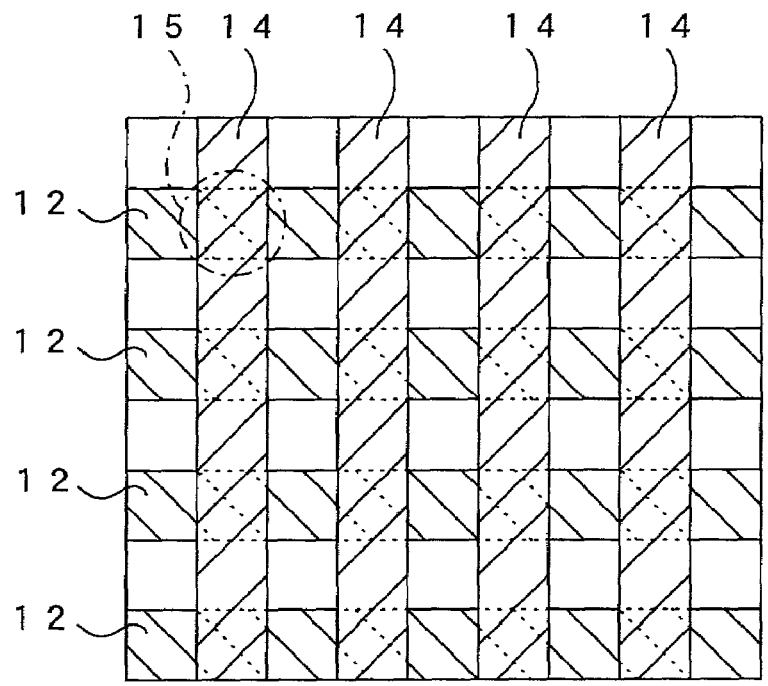
FIG. 2 is a plan view showing an arrangement of anodes and cathodes that constitute a display device in which organic EL elements shown in FIG. 1 are arranged in a matrix fashion.

As shown in FIG. 2, if the anodes 12 are formed like the stripe shape and the cathodes 14 are formed like the stripe shape in the direction that orthogonally intersects with the anodes 12, the display device in which a plurality of organic EL elements (intersecting portions of the anodes 12 and the cathodes 14) 15 are arranged on the glass substrate 11 in a matrix fashion can be constructed.

In this display device, like the simple-matrix liquid crystal display device, if the positive signal is supplied in sequence to a plurality of anodes 12 aligned in the vertical direction at a timing in synchronism with the horizontal synchronizing signal and also the negative signal is supplied in sequence to a plurality of cathodes 14 aligned in the horizontal direction within one horizontal synchronization period, desired images can be displayed on the organic EL display device.

Figure 3:
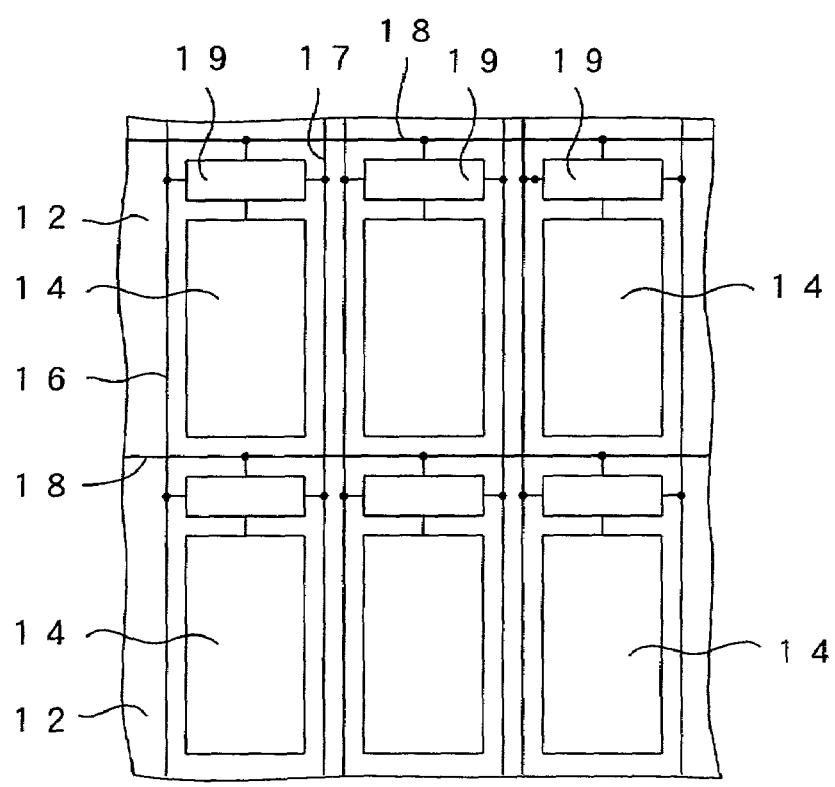
FIG. 3 is a plan view showing an example in which the organic EL elements shown in FIG. 1 are applied to an active-matrix organic EL display device.

Also, the present invention can be applied to the active-matrix organic EL display device shown in FIG. 3. More particularly, if the cathode 14 is formed every pixel and also the voltage applied to the cathodes 14 via switching elements 19, each being connected to a data line 16, a power supplying line 17, and a scanning line 18, is controlled every pixel, the desired images can be displayed on the organic EL display device. In this case, since the anode 12 is used as the common electrode for respective pixels, there is no necessity of the patterning.

In addition, in the above first embodiment, the case is explained where the organic EL layer 13 is directly formed on the anode 12 and the cathode 14 is directly formed on the organic EL layer 13. The buffer layer may be provided between the anode 12 and the organic EL layer 13 or between the organic EL layer 13 and the cathode 14.

(Second Embodiment)

FIGS. 4A to 4D are sectional views showing a method of manufacturing an organic EL element according to a second embodiment of the present invention.

The second embodiment shows an example of the organic EL element in which the buffer layer is provided between the anode and the organic EL layer.

Figure 4A:
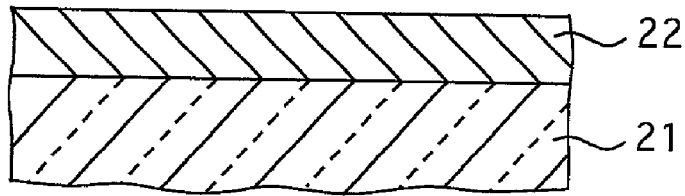
FIGS. 4A to 4D are views showing respective steps of manufacturing an organic EL element according to a second embodiment of the present invention in section.

First, as shown in FIG. 4A, the ITO film of 200 nm thickness is formed on an upper side of a glass substrate 21 by the sputter method to construct an anode (lower electrode) 22.

Figure 4B:
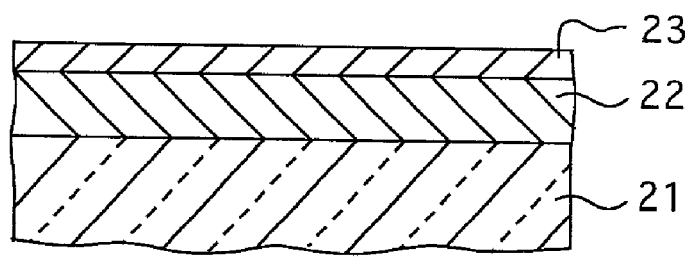
Figure 4C:
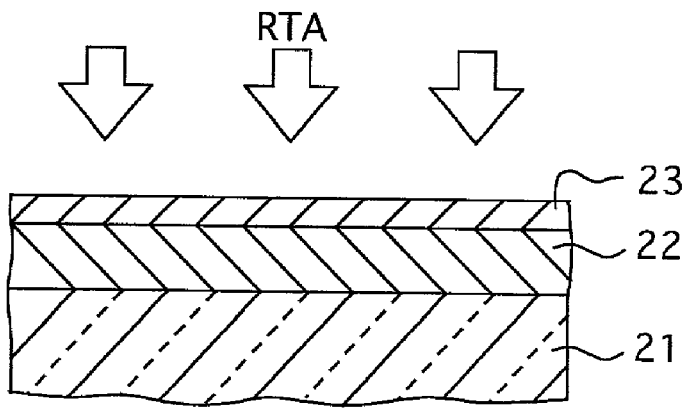

Then, as shown in FIG. 4B, the Ru (ruthenium) film of 30 nm thickness is formed on the anode 22 by the sputter method to construct a buffer layer 23. Then, as shown in FIG. 4C, the short-time annealing (RTA) is carried out at the temperature of 700° C. for 3 to 5 seconds by using the RTA (Rapid Thermal Annealing) equipment that heats by the lamp.

The Ru on the surface of the buffer layer 23 is oxidized by this short-time annealing. In this case, since RuO can be generated in a very short time, the particle size of the RuO is small and thus the situation that the large unevenness is formed on the surface of the buffer layer 23 can be avoided.

In this case, it is preferable that a thickness of the buffer layer 23 (the thickness before RTA) should be set smaller than 50 nm. This is because, if the thickness of the buffer layer 23 exceeds 50 nm, the light generated from an organic EL layer 24 is absorbed by the buffer layer 23 and thus the apparent luminescence intensity is lowered. Also, Mo or V as well as above Ru may be employed as the material of the buffer layer 23.

Figure 4D:
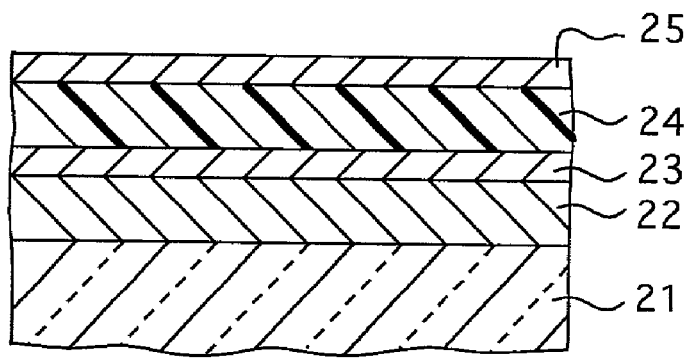

Then, as shown in FIG. 4D, the poly[3-(4-alkylphenyl) thiophene film of about 150 nm thickness is formed on the buffer layer 23 by the spin coating method to construct the organic EL layer 24. The material of the organic EL layer 24 is not limited to the above poly[3-(4-alkylphenyl) thiophene, and various organic EL materials of the monomer series or the polymer series may be employed.

Then, the AlLi film of about 20 nm thickness is formed on the organic EL layer 24 by the sputter method to construct a cathode (upper electrode) 25. Accordingly, the organic EL element according to the second embodiment can be completed. In this case, the material of the cathode 25 is not limited to the above AlLi, and the conductor containing the alkaline metal or the alkaline earth metal may be employed. Also, as described in the first embodiment, the cathode 25 may be formed to have the double-layered structure.

Actually measured results of the operating threshold voltage and the surface unevenness of the buffer layer after the above organic EL element is actually manufactured will be explained hereunder.

TDP/Alq$_3$ is employed as the material of the EL emission layer 24 and then the organic EL element is formed by the above methods, and then the operating threshold voltage is measured. As a result, an emission starting voltage is 7 V if no buffer layer 23 is provided whereas the emission starting voltage is 3.5 V if the buffer layer 23 is provided by the above method, whereby the reduction in the threshold voltage can be confirmed.

Also, when the unevenness of the surface of the buffer layer 23 is measured, such unevenness is 5 nm to 10 nm in the second embodiment. In contrast, in case RuO$_2$ is formed as the buffer layer by the sputtering, the unevenness of the surface of the buffer layer is 50 nm to 100 nm. As a result, the validity of the second embodiment can be checked.

According to the second embodiment, RuO, MoO, or VO that is effective to lower the operating threshold voltage is formed by forming the metal film of Ru, Mo, or V as the buffer layer 23 and then oxidizing the surface of the buffer layer 23 by the RTA. In this case, since the surface of the buffer layer 23 is oxidized in a short time, the situation that the large unevenness is formed on the surface of the buffer layer 23 can be avoided.

As a consequence, the short-circuit between the anode 22 and the cathode 25 can be avoided even if the thickness of the organic EL layer 24 is reduced, and thus the organic EL element having the low operating threshold voltage can be fabricated.

The second embodiment can be applied to the simple-matrix organic EL display device and the active-matrix organic EL display device, like the first embodiment.

In the second embodiment, the surface of the buffer layer 23 is oxidized by the RTA equipment that uses the lamp to heat. The surface of the buffer layer 23 may be oxidized by the laser beam irradiation, the plasma oxidation method, or the anodic oxidation method.

In case the surface of the buffer layer 23 is oxidized by the laser beam irradiation, the XeCl excimer laser is employed, for example. The surface of the buffer layer 23 is oxidized in a short time by scanning the laser beam, that is shaped into the rectangular shape having a narrow width, in the width direction. The energy of the laser beam is set to 390 mJ/cm$_2$, for example.

In case the surface of the buffer layer 23 is oxidized by the plasma oxidation method, such surface of the buffer layer 23 is exposed to the plasma containing the oxygen to oxidize the surface of the buffer layer 23. For example, the plasma oxidation process is performed by the RFO$_2$ plasma method under the conditions that the processing time is 10 minutes, the pressure is 40 Pa, and the power is 200 W.

In case the surface of the buffer layer 23 is oxidized by the anodic oxidation method, the mixed solution consisting of tartaric acid, ethylene glycol, and ammonia solution is employed as the electrolysis solution and the Pt (platinum) electrode is employed as the anode, for example. Then, the surface of the buffer layer 23 is anodic-oxidized by supplying a constant current of 5 mA to deposit a RuO$_2$ film.

The similar advantages such as the reduction in the operating threshold voltage, the avoidance of the formation of the uneven surface of the buffer layer, etc. can be achieved even when the surface of the buffer layer 23 is oxidized by any one of above methods.

(Third Embodiment)

FIGS. 5A to 5D are plan views showing manufacturing steps of an organic EL display device according to a third embodiment of the present invention.

This third embodiment shows an example of a method of manufacturing the full-color organic EL display device.

Figure 5A:
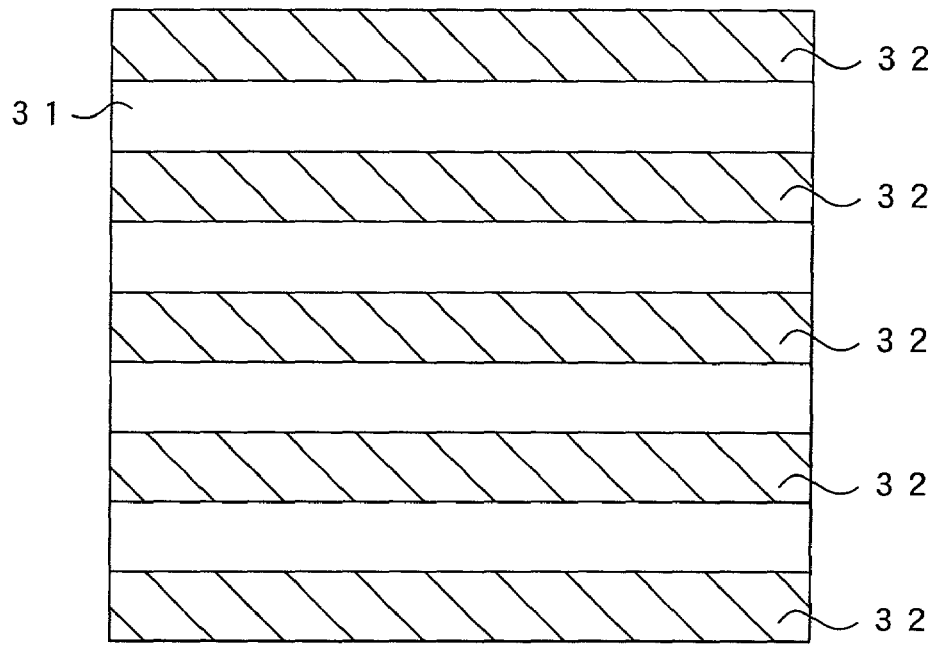
FIGS. 5A to 5D are views showing respective steps of manufacturing an organic EL display element according to a third embodiment of the present invention in plan.

First, as shown in FIG. 5A, an ITO film of about 200 nm thickness is formed by sputtering ITO on the overall upper surface of a glass substrate 31. Then, anodes (lower electrodes) 32 are formed by patterning the ITO film into a stripe shape by virtue of the photolithography. In this case, a width of the anode 32 is set to 20 μm, for example.

Then, an EL emission layer 33 is formed by forming poly[3-(4-alkylphenyl)thiophene] on the overall display area of the glass substrate 31 by virtue of the spin coating method to have a thickness of 1500 Å.

In the present invention, the material of the EL emission layer 33 is not limited to poly[3-(4-alkylphenyl) thiophene]. But such EL emission layer 33 must be formed of the polymer whose conjugate length can be changed by the light irradiation.

Figure 5B:
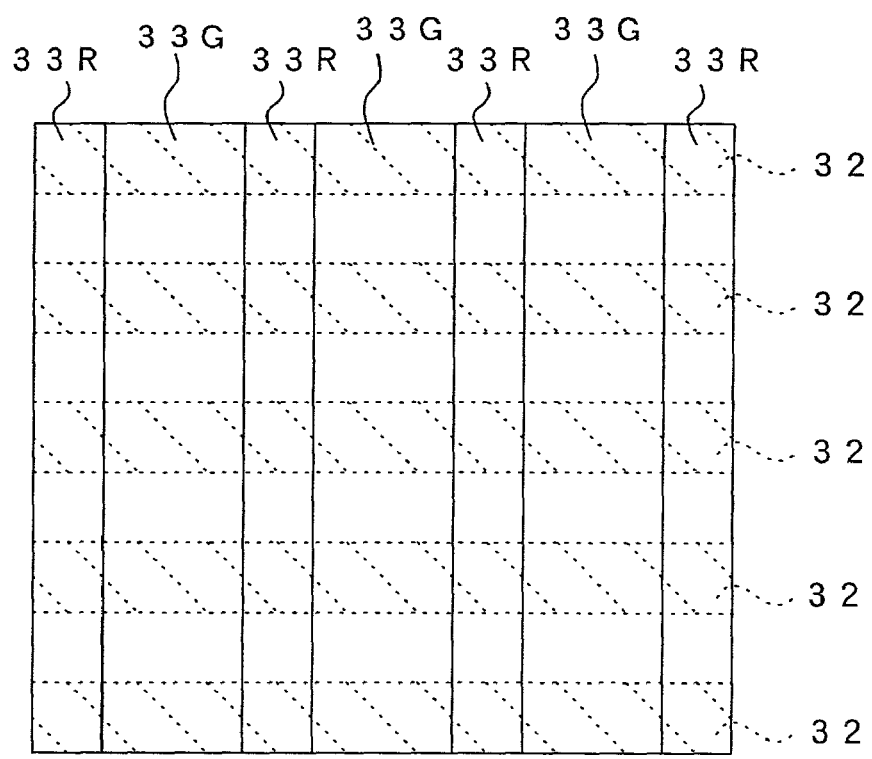

Then, as shown in FIG. 5B, the ArF laser beam is irradiated onto areas other than the red-color pixel area (R) (i.e., the green-color pixel area (G) and the blue-color pixel area (B)) under the condition of 1000 mJ/cm². As a result, the EL emission layer that is not subjected to the laser beam irradiation emits the red-color light (the wavelength of about 650 nm) whereas the EL emission layer that is subjected to the laser beam irradiation emits the green-color light (the wavelength of about 510 nm) because the conjugate length is shortened.

In FIG. 5B, the red-color light emitting portion of the organic EL layer is denoted by 33R and the green-color light emitting portion is denoted by 33G.

In this case, since the relationship between the irradiation intensity of the laser beam and the emitted color of the EL emission layer is different depending on the material of the EL emission layer, the laser beam irradiation conditions must be changed appropriately to meet the material.

Figure 5C:
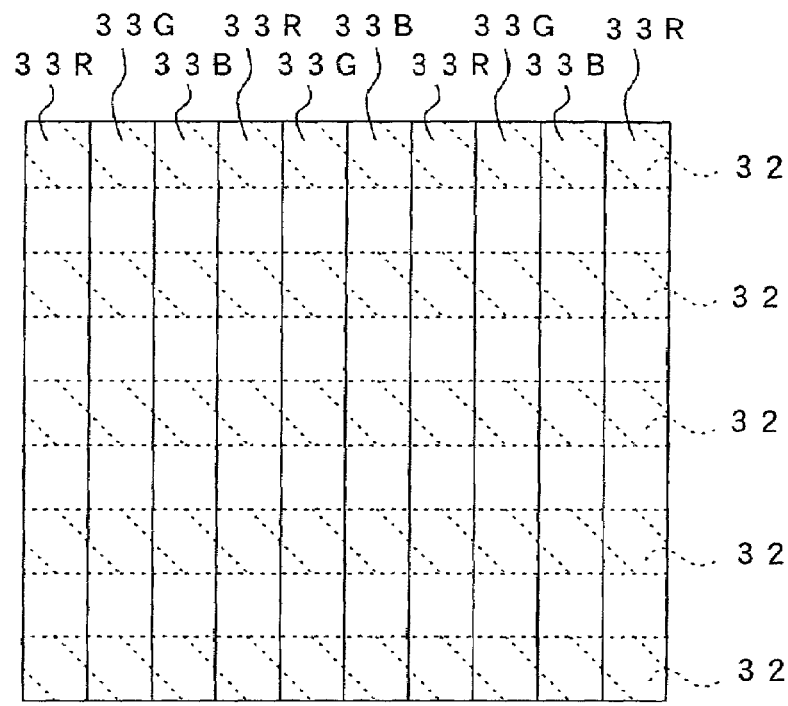

Then, as shown in FIG. 5C, the ArF laser beam is irradiated onto the blue-color pixel area of the EL emission device can be reduced. Thus, the full-color EL display device having three RGB-color pixels can be implemented.

In the third embodiment, the organic EL layer 33 is formed directly on the anodes (lower electrodes) 32, and then the cathodes (upper electrodes) 34 are formed directly on the organic EL layer 33. In this case, the buffer layer may be formed at least between the anodes 32 and the organic EL layer 33 and between the organic EL layer 33 and the cathodes 34.

In the third embodiment, the manufacturing method of the simple-matrix organic EL display device is explained. Also, the present invention can be applied to the manufacture of the active-matrix organic EL display device.

(Fourth Embodiment)

Next, organic EL material and a plane emission device and a display device using the same according to a fourth embodiment of the present invention will be explained with reference to FIG. 6 hereunder.

The organic EL material of the present invention can be expressed by a following general formula (4).

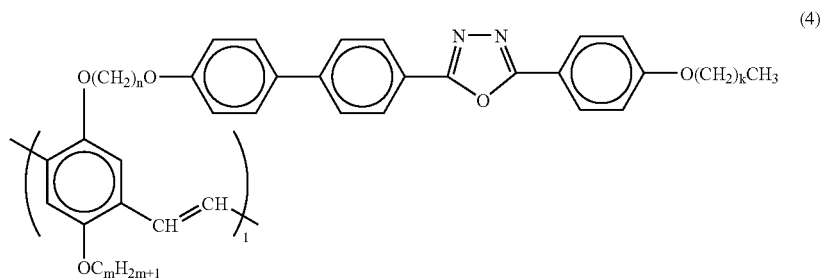

(4)

layer under the condition of 4000 mJ/cm². As a result, the EL emission layer that is subjected to the laser beam irradiation emits the blue-color light (the wavelength of about 460 nm) because the conjugate length is further shortened. In FIG. 5C, the blue-color light emitting portion of the organic EL layer is denoted by 33B.

Figure 5D:
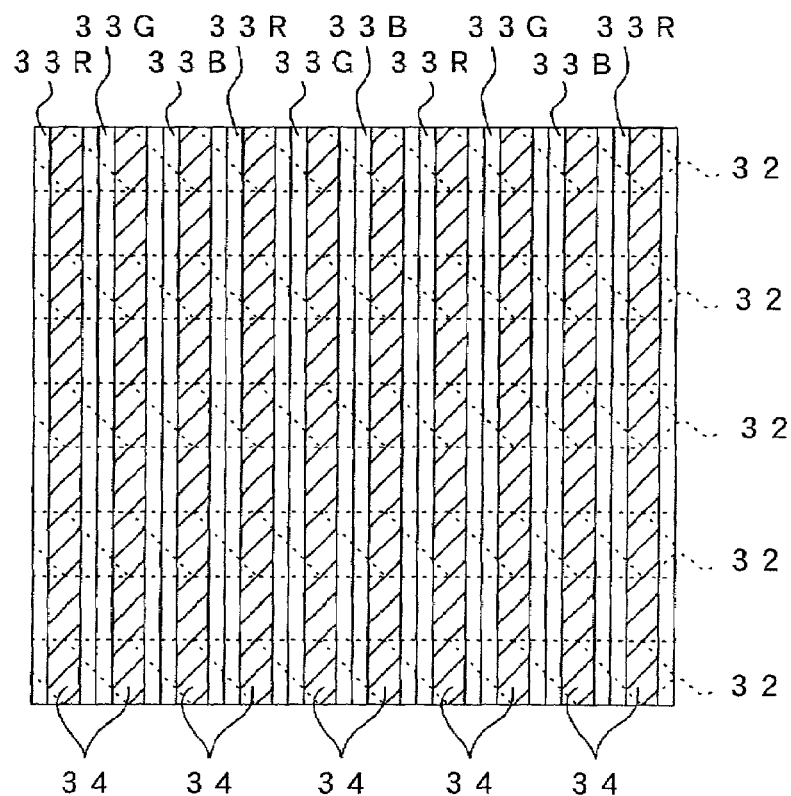

Then, as shown in FIG. 5D, cathodes (upper electrodes) 34 are formed on the EL emission layer 33 by the lift-off method. That is, photoresist is coated on the overall upper surface of the glass substrate, and then windows used to form the upper electrodes are opened in the resist film via exposing and developing steps. Then, AlLi is sputtered on the overall upper surface of the glass substrate to have a thickness of 200 nm, and then the AlLi film on the resist film is removed together with the resist. Thus, the cathodes 34 are formed.

The material of the cathodes 34 is not limited to above AlLi. Any conductor that contains the alkaline metal or the alkaline earth metal having the small work function may be employed.

In the third embodiment, as described above, the RGB-color emitting pixels are formed by using the polymer whose conjugate length can be changed by the laser beam irradiation to change the emitted color. In other words, since the multi-color emitting organic EL element can be formed not to employ the fine pattern technology such as the dry etching, etc., that requires the area separation of the organic EL layer 33 pixel by pixel, the number of manufacturing steps can be reduced and thus the production cost of the As apparent from the above general formula (4), a principal chain is constructed by the repetition unit consisting of the residue of the benzene, from which four hydrogen atoms are removed, and the vinylene group. Two side chains are bonded to the benzene ring constituting the principal chain.

One of the side chains is the univalent ether group having the carbon number m. Here m is an integer to satisfy the condition of $5 \leq m \leq 15$, and 1 is an integer to give the number of molecules of one hundred thousand to five millions.

Next, the chemical structure of the other of the side chains will be explained hereunder.

The alkylenedioxy group having the carbon number n, the biphenylene group, the residue of oxadiazole from which two hydrogen atoms are removed, the phenylene group, and the univalent other group having the carbon number k+1 are bonded in series to the benzene ring constituting the principal chain in this order.

This side chain portion has properties like the liquid crystal. Here n is an integer to satisfy the condition of $5 \leq n \leq 15$, and k is an integer to satisfy the condition of $5 \leq k \leq 15$. If k, m, n are set too small, the compound expressed by the general formula (4) is difficult to dissolve into the organic solvent. In contrast, if k, m, n are set too large, the synthesis of the compound becomes difficult.

Next, the method of synthesizing the organic EL material will be explained hereunder.

First, the benzene derivative expressed by a following general formula (5) is prepared.

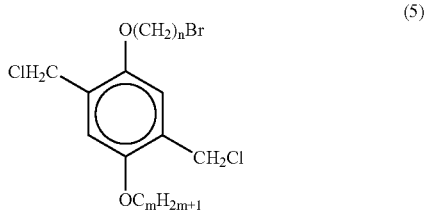

(5)

Also, the oxadiazole derivative expressed by a following general formula (6) is prepared.

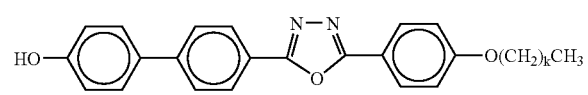

(6)

The compound expressed by a following general formula (7) is obtained by mixing the benzene derivative expressed by the above general formula (5) and the oxadiazole derivative expressed by the above general formula (6) and then adding the potassium hydroxide to the resultant solution.

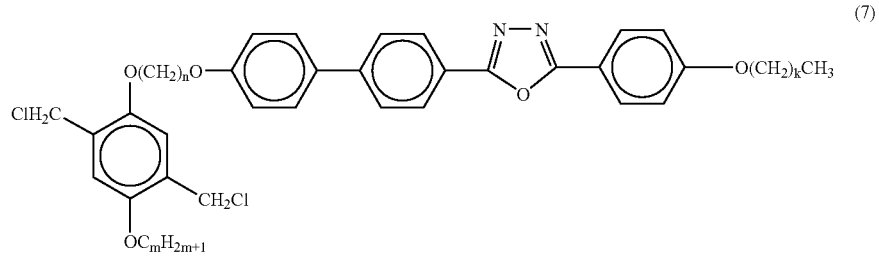

(7)

Further, the polymerization reaction is caused by adding KOC(CH$_3$)$_3$ to this compound. Thus, the organic EL material expressed by the above general formula (4) can be synthesized.

Next, a liquid crystal display device serving as the organic EL display device of the present invention employing the above organic EL material will be explained hereunder.

Figure 6:
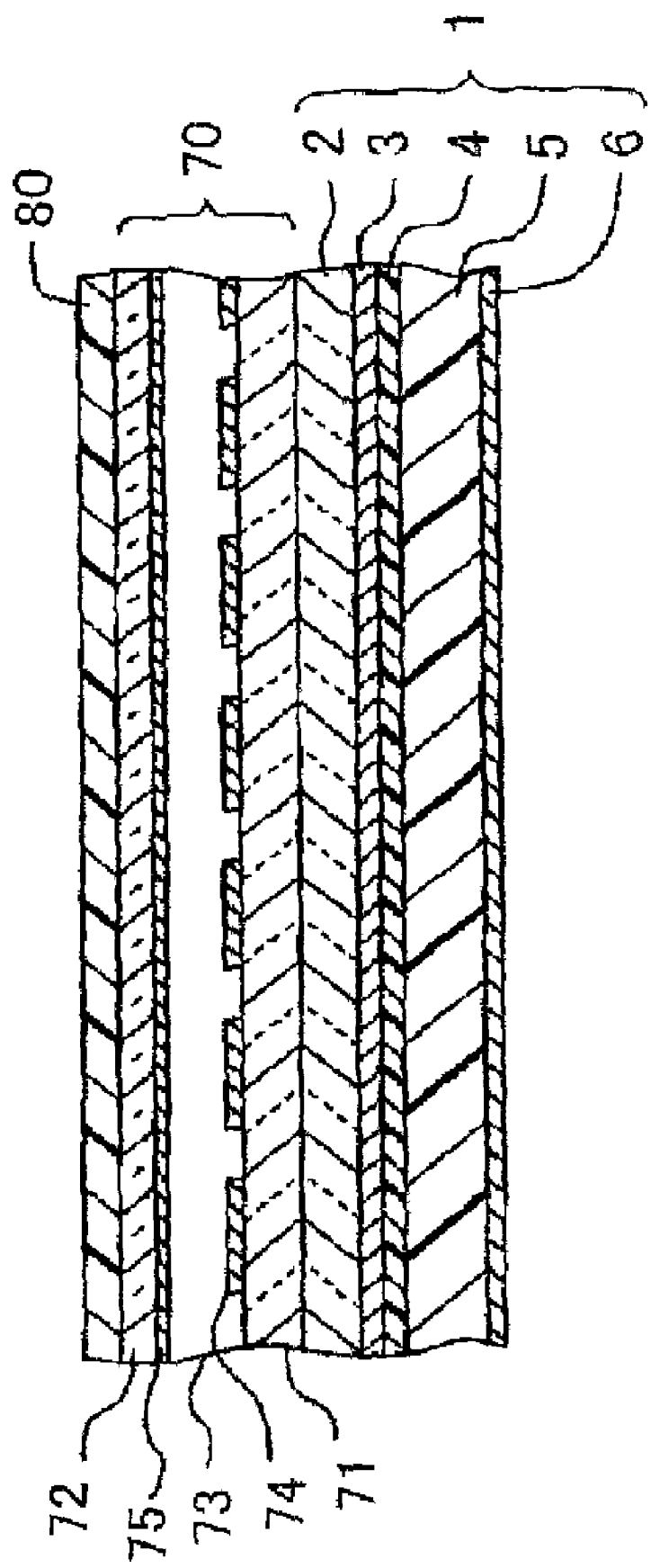
FIG. 6 is a sectional view showing the pertinent portion of a liquid crystal display device that is constructed by using organic EL elements according to a fourth embodiment of the present invention.

The liquid crystal display device shown in FIG. 6 in section is constructed to include a back-light panel 1, a liquid crystal panel 70, and a polarizing plate 80.

The back-light panel 1 has a laminated structure by stacking a transparent substrate 2, a transparent electrode 3, an alignment film 4, a luminous layer 5 and an electrode 6 in this order. The transparent electrode 3 is formed of the indium tin oxide (ITO), and its thickness is about 200 nm. The ITO film is formed by the sputtering.

The alignment film 4 is formed of the mixture consisting of poly 3,4-ethylenedioxythiophene (PEDOT) and polystyrenesulfonate (PSS). The alignment film 4 is formed by the spin coating method, and its thickness is about 200 nm. The rubbing process is applied to a surface of the alignment film 4. Polyaniline, etc. may be used as the material of the alignment film.

Next, a method of forming the luminous layer 5 will be explained hereunder.

The solution, in which the organic EL material expressed by the above general formula (4) is dissolved in the organic solvent such as toluene, chloroform, etc., is spin-coated on the surface of the alignment film 4. After the coating, the substrate is heated to exceed the mesomorphic temperature of the organic EL material and then is cooled down to the room temperature. When the temperature is in excess of the mesomorphic temperature, the side chain portions containing oxadiazole as the organic EL material expressed by the above general formula (4) are aligned in parallel with the rubbing direction of the alignment film 4.

When the substrate is cooled down to the room temperature into the solid state, this alignment state can be maintained without the influence of the external electric field, etc. The electrode 6 is a conductive film made of AlLi alloy having a thickness of about 300 nm. The AlLi alloy film is formed by the vacuum evaporation, etc., for example. The liquid crystal panel 70 is the active-matrix panel employing thin film transistors (TFTs), for example. Since the TFT liquid crystal panel has the well known structure, the outline thereof will be explained hereunder.

Transparent pixel electrodes 74 arranged in a matrix fashion are formed on an opposing surface of a TFT side transparent substrate 71. A transparent opposing substrate 72 is arranged in parallel with the TFT side transparent substrate 71 so as to oppose to the pixel electrodes 74.

A transparent common electrode 75 is formed on an opposing surface of the opposing substrate 72. A liquid crystal layer containing liquid crystal material is put between the TFT side transparent substrate 71 and the opposing substrate 72.

Although not shown in FIG. 6, an alignment film, TFTS, a black matrix, and others are formed. A rotating angle of a linearly polarized light, that propagate through a liquid crystal layer 73 in the thickness direction, can be controlled by applying the voltage between the pixel electrodes 74 and the common electrode 75.

The TFT side transparent substrate 71 is adhered to the transparent substrate 2 of the back-light panel 1. The polarizing plate 80 is adhered to an outer surface of the opposing substrate 72. If viewed along the direction perpendicular to the substrate surface, the polarization axis of the polarizing plate 80 intersects orthogonally with the rubbing direction of the alignment film 4.

Next, the operational principle of the liquid crystal display device shown in FIG. 6 will be explained hereunder.

When the carriers are injected into the luminous layer 5 by applying the DC voltage to both electrodes such that the electrode 6 act as the negative electrode and the transparent electrode 3 acts as the positive electrode, the polarized light is irradiated from the luminous layer 5 to the liquid crystal panel 70 side. The polarization direction of the irradiated light is in parallel with the alignment direction of the side chains containing oxadiazole in the above general formula (4), i.e., the rubbing direction of the alignment film 4.

If the polarized direction is not rotated when the polarized light passes through the liquid crystal panel 70, such polarized light does not pass through the polarizing plate 80 and thus the black display state is obtained. If the polarized direction is rotated by 90 degree, the polarized light passes through the polarizing plate 80 and thus the white display state is obtained. If the rotating angle is between 0 degree and 90 degree, the intermediate tone display state is obtained.

In the liquid crystal display device shown in FIG. 6, the polarized light is irradiated from the back-light panel 1. For this reason, no polarizing plate is arranged between the back-light panel 1 and the liquid crystal panel 70.

Therefore, the utilization factor of the irradiated light can be increased. Also, both the reduction in the consumption power and the reduction in size can be achieved rather than the case where the cold-cathode lamp is employed.

In the above fourth embodiment, the biphenylene group is bonded to the carbon atom on the principal chain side of oxadiazole in the above general formula (4). This biphenylene group may be replaced with the atomic group to which two or more phenylene groups and two or more cyclohexylene groups are bonded in total.

A general formula (8) shown in the following shows the case where the biphenylene group is replaced with the atomic group to which one phenylene group and one cyclohexylene group are bonded.

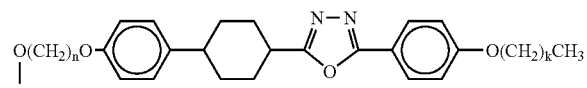

(8)

A general formula (9) shown in the following shows the case where the biphenylene group is replaced with the atomic group to which two phenylene groups and one cyclohexylene group are bonded like a chain.

Also, in the above fourth embodiment, the case is shown where one phenylene group is bonded to the carbon atom at the top end side of the side chain of the oxadiazole in the above general formula (4). This one phenylene group may be replaced with the atomic group to which two phenylene groups or more are bonded like a chain. Also, the case is explained where the benzene ring is contained in the principal chain of the organic EL material. The structure that the residue which is obtained by removing a part of hydrogen atoms from condensed polycyclic hydrocarbon, heterocyclic compound, or condensed heterocyclic compound is contained in addition to the benzene ring may be employed.

As an example of the condensed polycyclic hydrocarbon, there may be listed naphthalene, anthracene, or the like. As an example of the heterocyclic compound, there may be listed pyrrole, thiophene, furan, or the like. Also, as an example of the condensed heterocyclic compound, there may be listed carbazole, fluorine, or the like.

The present invention is not limited to the above embodiments, and various variations, modifications, and combinations may be applied.

What is claimed is:

1. An organic EL element comprising:
an organic EL layer formed between an anode and a cathode; and
said cathode consisting of a first conductive film that contacts to said organic EL layer and a second conductive film that constitutes a laminated structure together with said first conductive film, said first conductive film containing any one of an alkaline metal and an alkaline earth metal, and
said second conductive film containing any one of at least one type metal selected from the group consisting of Ru (ruthenium), Rh (rhodium), Ir (iridium), Os (osmium), Re (rhenium) and the oxides of Ru, Rh, Ir, Os and Re.

2. An organic EL element comprising:
an anode;
a buffer layer which is formed of at least one type metal selected from a group consisting of Ru, Mo, and V on said anode and a surface of which is oxidized, said buffer layer comprises said oxidized surface and an unoxidized layer under said oxidized surface;
an organic EL layer formed to be contacted to said oxidized surface of said buffer layer; and
a cathode formed on said organic EL layer.

3. An organic EL element according to claim 2, wherein said cathode contains any one of an alkaline metal and alkaline earth metal.

4. An organic EL element comprising:
an organic EL layer formed between an anode and a cathode; and
said cathode consisting of a first conductive film that contacts to said organic EL layer and a second conductive film that constitutes a laminated structure together with said first conductive film, said first conductive film containing any one of an alkaline metal and an alkaline earth metal, and said second conductive film is formed of a laminated film consisting of:
a conductive film containing any one of at least one type metal selected from the group consisting of Ru, Rh, Ir, Os, Re and the oxides of Ru, Rh, Ir, Os and Re, and
any one of a TiN film and a laminate film formed of a Ti film and a TiN film on said Ti film.

* * * * *